Dec. 24, 1974 W. H. JESSEL, JR., ET AL Plant Pat. 3671
CHRYSANTHEMUM PLANT
Filed Nov. 12, 1973
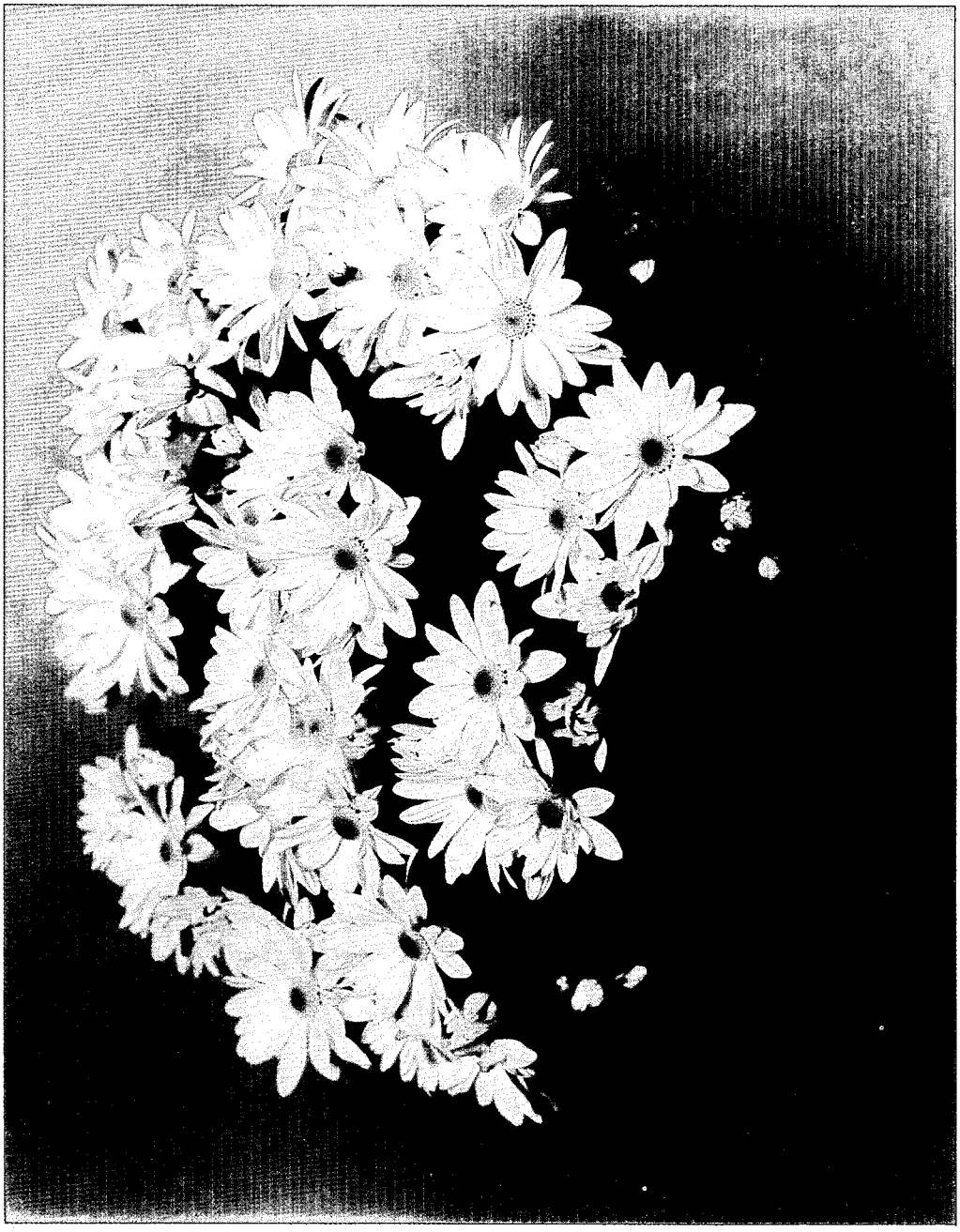

United States Patent Office

Plant Pat. 3,671
Patented Dec. 24, 1974

3,671

CHRYSANTHEMUM PLANT

Walter H. Jessel, Jr., Doylestown, and William E. Duffett, Akron, Ohio, assignors to Yoder Brothers, Inc., Barberton, Ohio

Filed Nov. 12, 1973, Ser. No. 415,211
Int. Cl. A01h *5/00*
U.S. Cl. Plt.—74 1 Claim

The present invention comprises a new and distinct cultivar of chrysanthemum plant known by the varietal name Yellow Garland which is a sport of the cultivar known in the United States as Garland. The parent cultivar is disclosed and claimed in our pending application Ser. No. 328,416, filed Jan. 31, 1973.

The new cultivar is similar in many respects to the parent cultivar Garland, having the same characteristics of:

1. General growth habit, vigor and foliage characteristics.
2. Flower size, form and permanence.
3. Flowering response and period of recommended value.
4. Grown as a tall treatment daisy pot mum.

The new cultivar is distinguished from Garland by its yellow flower color, as compared with the generally ivory flower color of Garland.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar, when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern United States, southeastern United States, southwestern United States and coastal California is January through December, and in southern Florida under outdoor conditions, October through April.

The accompanying photographic drawing shows the unique characteristics of the new cultivar, with the color being as nearly true as possible with color illustrations of this type. In the following description, color references are made to the Munsell Book of Color, 1963 edition (MBC) and the Munsell Cascade Limit Chart, 1972 edition (MLCC), and color comparisons are made with the parent cultivar Garland.

Botanical classification: *Chrysanthemum morifolium*, Ramat.

Bloom:
- *Size.*—3".
- *Fully expanded.*—3½".
- *Borne.*—Clusters on elongated pedicels.
- *Stems.*—Short and strong.
- *Form.*—Daisy.
- *Permanence.*—12–14 days.

| | Yellow Garland | Garland |
|---|---|---|
| *Color;* | | |
| Center of flower | Yellow-green, 2.5GY6/8 to yellow, 7.5Y8/12 (MBC). | |
| Base of petals | Light yellow-green, 2.5GY7/8 (MBC). | |
| Inside of petals | Medium yellow, 7.4Y8.7/9.6 (MLCC). | Light yellow, 10Y9/4 to ivory white, 10Y9/1 (MBC). |
| Reverse of petals | Medium yellow, 7.5Y8.8/7.2. | Ivory, 10Y9/2 to ivory white, 10Y9/1 (MBC). |
| Tonality from a distance. | Yellow | Ivory. |
| Discoloration | Medium yellow, 7.5Y8.8/7.2 (MLCC). | Ivory white, 10Y9/1 (MBC). |

Petals:
- *Texture.*—Smooth.
- *Appearance and form.*—Open at base, shallow multiridge keel, tapering to a blunt notched tip with recurved petal edges.
- *Arrangement.*—Composite, whorled on a single receptacle.
- *Persistence.*—Resists shatter.
- *Fragrance.*—Typical chrysanthemum.

Reproductive organs:
- *Stamen, anthers.*—250+.
- *Pollen.*—None.
- *Arrangement.*—Clustered in center of flower, if present.
- *Styles.*—Present both ray and disc florets.
- *Length.*—Short.
- *Ovaries.*—At the base of petal attached to receptacle.

Plant:
- *Form.*—Herbaceous.
- *Growth.*—Spreading.
- *Height.*—Approximately 12–15" when grown in a 4-cutting, 6" pot, given 9 week total treatment as defined in the timetables of Yoder Brothers, Inc., Barberton, Ohio, for the various seasons.
- *Spread.*—Approximately 16–20" when grown in a 4-cutting, 6" pot, given 9 week tall treatment as defined in the timetables of Yoder Brothers, Inc., Barberton, Ohio, for the various seasons.

Foliage:
- *Top side.*—Dark green, 7.5GY3/4 (MBC).
- *Size.*—Length to width ratio 16:11 with length up to 4" and width up to 2¾".
- *Quantity.*—Numerous.
- *Shape.*—Spatulate lobed.
- *Texture.*—Smooth.
- *Ribs and veins.*—Prominent.
- *Edge.*—Slightly indented.
- *Serration.*—Fine.
- *Under side.*—Medium green, 7.5GY5/4 (MBC).
- *Stipules.*—Prominent.

We claim:

1. A new and distinct cultivar of chrysanthemum characterized particularly as to its uniqueness when compared to the parent cultivar Garland by its yellow flower color.

No references cited.

ROBERT E. BAGWILL, Primary Examiner